United States Patent [19]
Webbers et al.

[11] Patent Number: 5,916,789
[45] Date of Patent: Jun. 29, 1999

[54] IMMOBILIZED ENZYME

[75] Inventors: Jos J.P. Webbers, Maassluis; John Krijgsman, Dordrecht, both of Netherlands

[73] Assignee: Genencor International, Inc., Rochester, N.Y.

[21] Appl. No.: 08/386,691

[22] Filed: Feb. 10, 1995

Related U.S. Application Data

[63] Continuation of application No. 08/055,119, Apr. 28, 1993, abandoned.

[30] Foreign Application Priority Data

Apr. 29, 1992 [EP] European Pat. Off. ............. 92-201194

[51] Int. Cl.$^6$ ........................... C12N 11/10; C12N 11/02; C12N 11/00; C12P 19/24
[52] U.S. Cl. ......................... 435/178; 435/177; 435/174; 435/94
[58] Field of Search ................................... 435/177, 178, 435/174, 94

[56] References Cited

U.S. PATENT DOCUMENTS

| | | | |
|---|---|---|---|
| 3,838,007 | 9/1974 | Van Velzen | 435/177 |
| 4,572,897 | 2/1986 | Amotz et al. | 435/177 |
| 4,604,354 | 8/1986 | Katz et al. | 435/94 |

FOREIGN PATENT DOCUMENTS

| | | |
|---|---|---|
| A-50 051 997 | 5/1975 | Japan . |
| A-59 109 173 | 10/1984 | Japan . |
| A-61 104 792 | 5/1986 | Japan . |
| A-61 031 085 | 6/1986 | Japan . |
| A-62-029 978 | 2/1987 | Japan . |

*Primary Examiner*—Francisco Prats
*Attorney, Agent, or Firm*—Debra J. Glaister

[57] ABSTRACT

An immobilized enzyme preparation is disclosed which comprises a gelling agent which has been cross-linked and active carbon in an amount of 1 to 3%. The gelling agent may be egg white chitosan or alginate. The enzyme glucose isomerase may be employed. When used in packed bed columns in enzymatic glucose isomerization processes, the disclosed immobilized enzyme formulation allows for a bedheight that is twice as high, a syrup flow that is doubled, or a doubled syrup viscosity when compared to formulations without carbon.

17 Claims, No Drawings

IMMOBILIZED ENZYME

PRIOR APPLICATION

This application is a continuation of U.S. patent application Ser. No. 055,119 filed Apr. 28, 1993, now abandoned.

BACKGROUND OF THE INVENTION (A) Field of the Invention

The present invention concerns an immobilized enzyme, the production thereof and its use.

(B) State of the Art

Nowadays several formulations of immobilized enzymes are commercially applied in production processes, one of the possibilities is an immobilization method for enzymes using e.g. gelatin and glutaric dialdehyde, see U.S. Pat. No. 3,838,007. Gelatin as gelling agent is often chosen because it is relatively cheap compared to other gelling agents and is abundantly available. Cross-linking with e.g. glutaric dialdehyde is carried out to obtain sufficiently rigid particles. In this way it was possible to immobilize non-proteolytic enzymes.

The immobilization process comprises the following steps:

- a crude enzyme containing biomass of about 4% (w/v) is mixed with a gelling agent and heated to slightly above the melting temperature of the gelling agent, for gelatin slightly above 40° C. The final concentration of the gelling agent is about 8% (w/v);
- the gelling agent-water-enzyme and/or microbial cells containing mixture is subsequently prilled into a cold, water-immiscible solvent e.g. butyl acetate;
- after collecting the coagulated spherical enzyme-containing particles several washings with a water-miscible organic solvent e.g. acetone or ethanol may be carried out in order to dehydrate partially the particles. The enzyme particles so formed keep their integrity at temperatures below 12–15° C.
- after these washings the excess of the organic solvent is removed by filtration, gravity sedimentation, centrifugation or decantation and the enzyme particles are resuspended in a mixture of cold water and acetone or ethanol and cross-linked with a bifunctional or polyfunctional protein reagent such as glutaric dialdehyde. For example glutaric dialdehyde in a concentration of 0.5–5% (v/v) is sufficient;
- finally, the excess of the cross-linking agent and other soluble impurities are washed out with water and the immobilized enzyme particles are either dried after dewatering with e.g. ethanol or dried directly in a fluid bed or tumbling drier or preferably transferred to a propylene glycol-water mixture and drained such that at least 25% (v/v) concentration has been reached in the particle.

Another method of immobilizing enzymes, cells and/or a combination thereof is described in U.S. Pat. No. 4,163,691. A mixture of a slurry of microbial cells containing glucose isomerase, an endocellular enzyme, at a temperature less than about 55° C. and 3 to 20 wt % of gelatin as a gelling agent passes a die to form threads into cold water which gels the threads. Instead of water, mixtures with organic solvents such as ethanol, methanol, acetone and water immiscible organic solvents such as ethylacetate, butylacetate and petroleum ether may be used which leads in many cases to reduced activity losses. The threads have a diameter of about 0.4 to 2 mm.

Subsequently the threads are cross-linked with 0.5 to 5% glutaric dialdehyde based on starting mass of the slurry and then cutting said cross-linked threads into pieces having a length of 0.4 to 10 mm.

An example is the preparation of an immobilized glucose isomerase on commercial scale. Also other enzymes with or without the presence of microbial cells may be immobilized with the use of this technique. As source of the enzyme glucose isomerase a strain of *Actinoplanes missouriensis* can be applied as described in U.S. Pat. 3,834,988. Submerged fermentation is carried out at neutral pH under aerobic conditions.

The immobilized glucose isomerase is applied in a plug flow or packed bed reactor at a temperature of 40 to 5° C. In this reactor glucose is converted into fructose during down flow passage over a column packed with immobilized enzymes. Packed beds of about 5 m high are often applied. The mechanical strength (compressibility) of the immobilized enzyme particles determines the pressure drop allowed over the column. When glucose isomerase immobilized in gelatin is used, the particles have a size of 1.4 mm or more for the prilling process and a diameter of 1.4 mm or more and a length of 2–10 mm for the extruded particles. Smaller particles would be deformed under influence of the pressure drop over the column and subsequently would plug the column whereas the use of larger particles would lead to low conversions because the rate limiting step of the conversion reaction is determined by the diffusion in the particles.

The above described system dates back to the early and mid 1970's and up to now no improvements to this system have been made. In order to obtain higher conversion rates, the particles should be smaller and therefore more rigid. It is the aim of the present invention to provide more rigid particles.

In order to obtain more rigid particles the following compounds were added to the immobilized enzyme particles to determine whether they increase the rigidity of the particles: aluminium oxides, silicates, sulphur, filter aids, casein, yeast cells, starch, agar, lignocellulose, alginate and pectins. However, none of these additives were found to be effective. Often prilling or extruding of enzyme/gelling agent/additive was less effective due to high viscosities or surface tension changes. In some cases even weaker particles were formed.

SUMMARY OF THE INVENTION

We have now surprisingly found that the incorporation of active carbon, preferably in powder form into the particles, improves considerably the strength of the particles. Accordingly, the present invention provides an immobilized enzyme formulation which comprises a gelling agent having cross linkages and active carbon. Therefore the enzyme is immobilized in a matrix consisting of a gelling agent which is cross-linked and active carbon.

The present invention also provides a process for the preparation of an immobilized enzyme which comprises the following steps (a) fermenting a strain of microorganism to produce a broth containing the enzyme;

(b) adding a gelling agent to the broth formed in step (a);

(c) adding 1 to 5% (w/v) active carbon;

(d) forming an enzyme-gelling agent preparation in particulate form; and (e) cross-linking the gelling agent.

This process results in a gelling agent whereby the enzyme as well as the carbon is homogeneously distributed through the gelling agent.

According to one aspect of the invention the particle diameter can be reduced to 1.3 to 0.6 mm, preferably 1.2 to 0.8 mm in the reactor column without unacceptable deformation of the particles. The increase in strength of the particles allows smaller particles to be used without the risk of clogging the column under application conditions.

According to another aspect of the invention the activity per reactor volume is increased because of the use of these smaller particles. Another advantage of the use of active carbon is that the apparatus used for the preparation of the immobilized enzyme does not have to be substantially altered.

DETAILED DESCRIPTION OF THE INVENTION

The active carbon is introduced during the preparation of the immobilized enzyme, for example just before the prilling or extruding step.

All kinds of active carbons can be used. In some cases however they should be food grade and compatible with the enzyme involved. It should preferably not contain impurities which are not inert with respect to the substrate. The active carbon is generally in the form of a powder, having particle size of 500 µm or less, preferably the particle size is smaller than 250 µm.

The amounts of the active carbon and gelling agent in the mixing step determine the product formed: when too small quantities of the gelling agent are added, the mixture does not solidify, when too much gelling agent is added, the mixture becomes too viscous. For example in case of gelatin:

less than 3% (w/v) gelatin, the solution does not coagulate during prilling;
more than 10% (w/v) gelatin, the solution is too viscous.

With respect to the carbon addition:

1% (w/v) of active carbon already gives an improvement in the strength of the formed particle;
more than 5% (w/v) of active carbon: the solution becomes too viscous.

Therefore usually 3 to 10% (w/v) of gelling agent and 1–5% (w/v) of active carbon, preferably 3% (w/v) of active carbon is present in the enzyme-containing liquid to be processed, for example by prilling.

The enzyme concentration is related to the biomass present which is 2 to 10% (w/v), a fermentation broth containing more than 10% (w/v) biomass may be too viscous depending on the type of micro-organism applied and would require an extra viscosity reduction step whereas micro-bial cell concentrations of less than 2% (w/v) may result in adversely low viscosities and low enzyme concentrations. As enzyme sources can be applied all industrial strains derived from yeasts, molds and bacteria, preferably Streptomyces, Actinoplanes and Bacillus species. The concentration of the enzyme in the particles depends on the kind of enzyme and its use.

For glucose isomerase the activity range will be on the order of 20 to 500 Units/gram immobilized material under standard conditions. 1 Unit is defined as the amount of enzyme which isomerizes initially in 1 hour one gram of glucose dry substance into a glucose/fructose mixture with a fructose content of 45% under downflow column operative conditions (60° C.). Before the enzyme or microorganisms are mixed with the gelling agent, the enzyme or microorganisms are preferably heat-treated (e.g. pasteurized) to kill the microorganisms present.

In case of extrusion, the process is more flexible with respect to viscosities. Gelling agents up to 20 wt % and microbial cells up to 20 wt % and active carbon up to 10 wt % can be used.

It will be appreciated that all kinds of forms of the immobilized enzyme can be produced. The particulate form may be a form of spherical or almost spherical particles, but, although the specification generally refers to those spherical or almost spherical particles, the particulate form may also be the form of, for example, rods or fibers, e.g. extruded rods. In general, 'particulate form' means a form of the enzyme preparation having granular particles of from 0.6 to 1.3 mm, preferably from 0.8 to 1.2 mm or rod-shaped particles of from 0.4 to 1.5 mm in diameter and 2 to 10 mm in length.

The term 'gelling agent' used herein means a compound of which an aqueous solution may be transformed into a solid or semi-solid state by special treatment, e.g. by cooling when gelatin is used, or heating when fresh egg white is used or a pH decrease in case of chitosan which flocculates at a pH below 6. Gelling agents which may be used according to the present invention include gelatin, egg white, chitosan, alginates or a mixture thereof. Preferably gelatin is used. Gelling agents are applied which are not broken down or deteriorated by the enzyme in question and which do not deactivate the enzyme. For example, when proteolytic enzymes are immobilized, the gelling agent cannot be a protein.

Examples of suitable enzymes which may be used are invertases, amyloglucosidases, lactases, maltases, amylases, ureases, lipases, esterases, glucose isomerases, glucose oxidases, dehydrogenases, L-amino acylase, L-aspertase and penicillinases. Preferably the enzyme is glucose isomerase. More preferably the glucose isomerase originates from a strain of Actinomycetes preferably of the genus Actinoplanes or Streptomyces. Most preferably the glucose isomerase is obtained from *Actinoplanes missouriensis*. Mixtures of enzymes may also be employed in the process so that the resulting enzyme-gelling agent particles can be utilised for carrying out two or more enzymatic reactions simultaneously. Also insoluble enzymes may be employed such as when they are in an unfavorable form, e.g. a powder and microorganisms and even spores containing enzymes may be employed in the process.

The enzyme-gelling agent mixture which is used in the process as a starting material may be prepared by dissolving or suspending the enzyme in an aqueous gelling agent solution. The temperature of the aqueous gelling agent solution is dependent on the range of temperatures over which the enzyme remains active. Therefore, a temperature of about 20° C. to 50° C. is preferred for most enzymes, the maximum temperature is generally about 60° C. to 65° C., but higher temperatures may be employed for enzymes which are active above 65° C.

The cross-linking step is carried out with a bi- or polyfunctional protein reagent which forms covalent bonds with the enzyme and/or the gelling agent. Examples of suitable bifunctional reagents are cross-linking agents, for example aldehydes such as glutaric dialdehyde, acrolein or crotonaldehyde, esters such as chloroformic acid esters, acid halides such as acid chlorides, epoxides such as epichlorohydrin, derivatives of dimethyladipic acid, carbodiimides, phenol-2,4-disulphonyl chloride, bromocyanide, activated agents such as bromocyanide-activated compounds of acid halides, or mixtures of two or more of those compounds. Preferably, an aqueous solution of glutaric dialdehyde is employed at temperatures from 5 to 20° C., preferably 10 to 15° C., and reaction times of 10 to 120 minutes, preferably 15 to 60 minutes more preferably about 30 minutes.

According to one embodiment of the invention, the enzyme-gelling agent particles are dehydrated. Suitable dehydration agents are liquids having a high solubility in water or are miscible with water and they must be compatible with the enzyme. Examples of suitable dehydration agents are alcohols with up to three carbon atoms such as methanol, ethanol or isopropanol, acetone, or a mixture of two or more of those compounds. Dehydration is generally carried out at a temperature of 5 to 20° C., preferably at about 10° C. The cross-linking bi- or polyfunctional reagent may be added to this liquid or applied to the particles after the dehydration step. The dehydration step may be carried out prior to or after separation of the particles from the organic liquid used for the suspension step. The dehydration step reduces the size of the enzyme-gelling agent particles, and improves the cross-linking reaction when the dehydrated particles are brought into an aqueous/organic solution of the bi- or polyfunctional reagent. After the dehydration step, the enzyme-gelling agent particles generally have a particle size of from 0.5 to 1.3 mm.

Finally, the enzyme-gelling agent preparations obtained in particulate form according to the invention are preferably washed. Examples of suitable washing liquids are water or buffered solutions having a pH depending on the enzyme. Generally, drying of the preparation in particulate form is not necessary, but in special cases a drying step may be included. In general, the temperature of the washing step is 5 to 30° C., preferably about 15° C. In general the temperature of the drying step is 30 to 60° C., preferably about 40° C. For special applications, the cross-linking step may be repeated for optimal physical properties.

The water-insoluble enzyme-gelling agent preparations in particulate form according to the invention may be used in columns or reactors for example. The enzyme-gelling agent particles can be separated easily from the reaction mixture and may be used repeatedly.

The water-insoluble, enzyme-gelling agent preparations in particulate form, may in general be used in all processes where soluble enzyme is conventionally used. For example, invertase-gelling agent particles may be used for the inversion of saccharose and amyloglucosidase may be used for the hydrolysis of starch and dextrines, as in beer manufacturing. Further the water-insoluble enzyme-gelling agent preparations of the present invention in particulate form may be used in cases where soluble enzymes cannot be used economically or may be applied for other reasons. Apart from the improvement in strength, another advantage of the addition of carbon is that the carbon decolours the processing liquids and product during application to a certain extent. The decoloured processing liquids may thus be recycled more easily. For example, a distillation column used for recycling of dehydrating agents, requires less cleaning when carbon containing particles are used.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit and scope of the appended claims.

The following experimental data are given to illustrate the invention. It has to be understood that a person skilled in the art who is familiar with the methods may use other glucose isomerase producing strains which can be equally used for the purpose of the present invention. These alterations are included in the scope of the invention.

EXAMPLE 1

To a fermentation-mash of *Actinoplanes missouriensis* NRRL B-3342 (U.S. Pat. No. 3,834,988) containing 4.5% cell-solids and glucose isomerase, was added under agitation at room temperature:

|   | % active carbon | % gelatin dry powder |
|---|---|---|
| A | 0 | 8.1 |
| B | 1.0 | 7.4 |
| C | 2.0 | 6.7 |
| D | 3.0 | 6.0 |

The active carbon was added in powder form (99% of the carbon has a particle size of less than 250 $\mu$m). After heating up this mixture to 40° C. to melt the gelatin, the mixtures were prilled by the earlier described method (U.S. Pat. No. 3,838,007) in cold (10° C.) butylacetate and afterwards cross-linked with 3.5% glutaric aldehyde during 30 min at 10° C. All four batches were tested in the standard packed bed column flow test with 45% glucose syrup at 60° C.

The resistance to flow may be calculated as follows for rigid particles:

$$V_s H \eta = \frac{\Delta P \, \epsilon^3 d_p^2}{180(1-\epsilon)^2} \tag{1}$$

Plotting $\Delta P$ as function of $V_s$ (syrup flow), H (bed height) $\eta$ (syrup viscosity) yields a straight line. For deformable particles however the void fraction ($\epsilon$) is a function of the pressure applied. It can be proven mathematically that the pressure drop across a packed bed containing deformable particles can be calculated using the following expression:

$$V_s H \eta = K_1 (1 - e^{-K_2 \Delta P}) \tag{2}$$

in which we assume a exponential decay of the porosity as function of the local pressure applied.

$K_1$ and $K_2$ are constants to be determined experimentally. The initial slope of the curve is given by the product of these constants. The higher this value the less resistance to flow. The higher the $K_2$-value the higher the allowable pressure drop across the column.

Based on the experimental values of $K_1$ and $K_2$ Table 1 gives the results of the $V_s H \eta$ values at a pressure drop over the column of 0.8 bar.

TABLE 1

|   | % carbon | $V_s H \eta$ at 0.8 bar |
|---|---|---|
| A | 0 | $3.0*10^{-5}$ |
| B | 1 | $5.3*10^{-5}$ |
| C | 2 | $5.3*10^{-5}$ |
| D | 3 | $6.3*10^{-5}$ |

The results indicate a doubled $V_s H \eta$ value in case of 3% carbon which means that application of this product in packed bed columns allows either for a bedheight that is twice as high, a syrup flow that is doubled or a doubled syrup viscosity, compared to the product without carbon.

EXAMPLE 2

*Streptomyces lividans* GIT 101 produces a protein-engineered variant of *Actinoplanes missouriensis* glucose isomerase, in which lysine at position 253 of the amino acid sequence of the enzyme is replaced by arginine (EP 0351029, Bio/Technology 9 (8) 738, 1991). *Streptomyces lividans* GIT 101 was obtained by transformation of *Streptomyces lividans* TK21 (John Innes Institute, Norwich, UK) with plasmid pWGx.GIT; this plasmid consists of the replication functions and thiostrepton resistance gene of the well known vector pIJ702 (Katz et al., J. Gen. Microbiol. 129, 2703, 1983) and a 1.7 kb insert encoding the mutant glucose isomerase GIT.

A sample of *Streptomyces lividans* GIT 101 has been deposited with the CBS on Apr. 28, 1992 under the accession number CBS 223.92.

To one part of a fermentation mash of *Streptomyces lividans* (GIT 101) containing 4% cell-solids and glucose isomerase, was added under agitation 6% of gelatin, to another part was added 3% active carbon and 6% of gelatin.

After heating to 40° C., prills were produced from both parts by the earlier described method and tested in the standard packed bed test column.

Table 2 gives the results of the $V_sH\eta$ values at a pressure drop over the column of 0.8 bar.

TABLE 2

|  | $V_sH\eta$ at 0.8 bar |
|---|---|
| without carbon | $4.5*10^{-5}$ |
| with 3% carbon | $9.1*10^{-5}$ |

The results indicate a doubled $V_sH\eta$ value in case of 3% carbon which means that application of this product in packed bed columns allows either for a bedheight that is twice as high, a syrup flow that is doubled or a doubled syrup viscosity, compared to the product without carbon.

What is claimed is:

1. An enzyme formulation comprising an enzyme, a gelling agent having cross-linkages and active carbon whereby the enzyme and the active carbon are homogeneously distributed through the gelling agent, said gelling agent comprising gelatin, egg white, chitosan or alginate, and whereby the active carbon is present in a quantity of from 1% to 3%, weight/volume, wherein said enzyme formulation has improved particle strength compared to an immobilized enzyme composition identical to said enzyme formulation except for the absence of said active carbon.

2. The formulation of claim 1 whereby the gelling agent has cross-linkage with a bi- or polyfunctional cross-linking reagent which forms covalent bonds with the enzyme and/or the gelling agent.

3. The formulation according to claim 2 wherein the cross-linking reagent is glutaric dialdehyde.

4. A formulation of claim 1 in granular form.

5. A formulation of claim 1 which has a rod shaped form.

6. A formulation of claim 1 wherein the enzyme is at least one member of the group consisting of invertase, amyloglucosidase, lactase, maltase, amylase, urease, lipase, esterase, glucose isomerase, glucose oxidase, dehydrogenase, penicillinase, L-amino acylase and L-aspartase.

7. A formulation according to claim 6 wherein the enzyme is glucose isomerase obtainable from a strain of Actinomycetes.

8. A formulation according to claim 7 wherein the strain of Actinomycetes is *Actinomyctes missouriensis*.

9. A formulation according to claim 1 wherein the gelling agent is gelatin.

10. A formulation of claim 1 wherein the active carbon has a particle size smaller than 500 µm.

11. A formulation of claim 1 which contains 3% (w/v) of active carbon.

12. A formulation of claim 1 which contains from 3 to 20% (w/v) of gelling agent.

13. A formulation according to claim 1 which contains from 2–10% enzyme containing biomass.

14. A formulation of claim 4 wherein the granular form has a particle size of 0.6 to 1.3 mm.

15. A formulation of claim 5 wherein the rod-shaped form has a diameter of 0.8 to 1.5 mm and a length of 2 to 10 mm.

16. A formulation of claim 7 wherein the Actinomycetes strain is of the genus Actinoplanes or Streptomyces.

17. A process for the preparation of an immobilized enzyme which comprises the following steps:

(a) fermenting a strain of microorgansims to produce a broth containing the enzyme;

(b) adding a gelling agent selected from the group consisting of gelatin, egg white, chitosan and alginate to the broth formed in step (a);

(c) adding 1 to 3% (w/v) active carbon;

(d) forming an enzyme-gelling agent preparation in particulate form; and (e) cross-linking the gelling agent.

* * * * *